United States Patent
Weingartner et al.

(10) Patent No.: US 10,775,464 B2
(45) Date of Patent: Sep. 15, 2020

(54) SYSTEM AND METHOD FOR DYNAMIC, CARDIAC PHASE-RESOLVED QUANTITATIVE LONGITUDINAL RELAXATION PARAMETER MAPPING

(71) Applicant: REGENTS OF THE UNIVERSITY OF MINNESOTA, Minneapolis, MN (US)

(72) Inventors: Sebastian Weingartner, Minneapolis, MN (US); Mehmet Akcakaya, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 96 days.

(21) Appl. No.: 15/885,158

(22) Filed: Jan. 31, 2018

(65) Prior Publication Data
US 2018/0217217 A1 Aug. 2, 2018

Related U.S. Application Data (60) Provisional application No. 62/452,733, filed on Jan. 31, 2017.

(51) Int. Cl.
| | | |
|---|---|---|
| G01R 33/56 | (2006.01) | |
| G01R 33/50 | (2006.01) | |
| A61B 5/00 | (2006.01) | |
| G01R 33/48 | (2006.01) | |
| A61B 5/055 | (2006.01) | |
| G01R 33/561 | (2006.01) | |
| G01R 33/565 | (2006.01) | |

(Continued)

(52) U.S. Cl.
CPC ........ *G01R 33/5602* (2013.01); *A61B 5/0044* (2013.01); *G01R 33/50* (2013.01); *A61B 5/055* (2013.01); *G01R 33/246* (2013.01); *G01R 33/4828* (2013.01); *G01R 33/5601* (2013.01); *G01R 33/5613* (2013.01); *G01R 33/5673* (2013.01); *G01R 33/56509* (2013.01)

(58) Field of Classification Search
CPC .............. G01R 33/5602; G01R 33/567; G01R 33/5673; G01R 33/48; G01R 33/50; G01R 33/5613
USPC .................................................. 324/300–322
See application file for complete search history.

(56) References Cited

U.S. PATENT DOCUMENTS

| | | | |
|---|---|---|---|
| 6,796,293 B2 * | 9/2004 | Bayerle ................... | F02N 11/04 123/179.3 |
| 7,446,526 B2 * | 11/2008 | Cunningham ....... | G01R 33/246 324/307 |

(Continued)

OTHER PUBLICATIONS

Yaman et al., Locally Low-Rank Tensor Regularization for High-Resolution Quantitative Dynamic MRI, 2017 IEEE 7th International Workshop on Computational Advances in Multi-Sensor Adaptive Processing (CAMSAP) (Year: 2017).*

(Continued)

*Primary Examiner* — Patrick Assouad
*Assistant Examiner* — Sean Curtis
(74) *Attorney, Agent, or Firm* — Quarles & Brady LLP (57) ABSTRACT

Systems and methods for producing quantitative maps of a longitudinal relaxation parameter, such as a longitudinal relaxation time ("T1"), using magnetic resonance imaging ("MRI") are described. More particularly, a pulse sequence and imaging method for cardiac phase-resolved myocardial T1 mapping are provided.

23 Claims, 4 Drawing Sheets

(51) Int. Cl.
*G01R 33/24* (2006.01)
*G01R 33/567* (2006.01)

(56) References Cited

U.S. PATENT DOCUMENTS

| | | | | |
|---|---|---|---|---|
| 9,008,753 B2* | 4/2015 | Messroghli | ........ | G01R 33/4818 |
| | | | | 324/309 |
| 9,129,424 B2* | 9/2015 | Xue | ........ | G06T 11/003 |
| 9,395,431 B2* | 7/2016 | Detsky | ........ | A61B 5/055 |
| 9,835,705 B2* | 12/2017 | Weingartner | ........ | A61B 5/055 |
| 10,168,405 B2* | 1/2019 | Kang | ........ | G01R 33/50 |
| 10,197,656 B2* | 2/2019 | Hilbert | ........ | G01R 33/50 |
| 10,264,994 B2* | 4/2019 | Spottiswoode | ........ | A61B 5/055 |
| 10,386,429 B2* | 8/2019 | Rodgers | ........ | G01R 33/50 |
| 10,451,700 B2* | 10/2019 | Weingartner | ........ | G01R 33/5607 |
| 10,520,570 B2* | 12/2019 | Weingartner | ........ | G01R 33/543 |
| 10,552,955 B2* | 2/2020 | Hu | ........ | G01R 33/5611 |
| 2003/0150430 A1* | 8/2003 | Bayerle | ........ | F02N 11/08 |
| | | | | 123/491 |
| 2005/0245809 A1* | 11/2005 | Wolff | ........ | G01R 33/561 |
| | | | | 600/410 |
| 2008/0150528 A1* | 6/2008 | Cunningham | ........ | G01R 33/246 |
| | | | | 324/309 |
| 2009/0275822 A1* | 11/2009 | Detsky | ........ | A61B 5/055 |
| | | | | 600/413 |
| 2015/0123659 A1* | 5/2015 | Weingartner | ........ | A61B 5/055 |
| | | | | 324/309 |
| 2015/0285879 A1* | 10/2015 | Hilbert | ........ | G01R 33/5619 |
| | | | | 324/309 |
| 2015/0323630 A1* | 11/2015 | Weingartner | ........ | G01R 33/543 |
| | | | | 324/309 |
| 2016/0131729 A1* | 5/2016 | Kang | ........ | G01R 33/50 |
| | | | | 324/309 |
| 2016/0139225 A1* | 5/2016 | Basha | ........ | G01R 33/50 |
| | | | | 324/309 |
| 2016/0291106 A1* | 10/2016 | Fuderer | ........ | G01R 33/4824 |
| 2017/0293005 A1* | 10/2017 | Panther | ........ | G01R 33/445 |
| 2017/0307699 A1* | 10/2017 | Rodgers | ........ | G01R 33/56527 |
| 2017/0325707 A1* | 11/2017 | Spottiswoode | ........ | A61B 5/055 |
| 2018/0067184 A1* | 3/2018 | Weingartner | ........ | G01R 33/50 |
| 2018/0217217 A1* | 8/2018 | Weingartner | ........ | G01R 33/5602 |
| 2018/0286041 A1* | 10/2018 | Hu | ........ | G06T 11/008 |
| 2019/0049538 A1* | 2/2019 | Panther | ........ | A61B 5/00 |
| 2019/0064294 A1* | 2/2019 | Neji | ........ | G01R 33/246 |
| 2019/0154785 A1* | 5/2019 | Zhou | ........ | G01R 33/56325 |
| 2019/0285711 A1* | 9/2019 | Keupp | ........ | G01R 33/50 |
| 2019/0369189 A1* | 12/2019 | Huang | ........ | G06T 11/005 |
| 2020/0041591 A1* | 2/2020 | Weingartner | ........ | A61B 5/7289 |
| 2020/0072931 A1* | 3/2020 | Zaiss | ........ | G06N 20/10 |

OTHER PUBLICATIONS

Weingartner et al., Temporally Resolved Parametric Assessment of Z-Magnetization Recovery (TOPAZ): Dynamic Myocardial T1 Mapping Using a Cine Steady-State Look-Locker Approach. Magnetic Resonance in Medicine 79:2087-2100 (2018) (Year: 2018).*

Kargas et al., Low-Rank Tensor Regularization for Improved Dynamic Quantitative Magnetic Resonance Imaging. (Year: 2016).*

* cited by examiner

SYSTEM AND METHOD FOR DYNAMIC, CARDIAC PHASE-RESOLVED QUANTITATIVE LONGITUDINAL RELAXATION PARAMETER MAPPING

CROSS-REFERENCE TO RELATED APPLICATIONS

This application claims the benefit of U.S. Provisional Patent Application Ser. No. 62/452,733, filed on Jan. 31, 2017, and entitled "SYSTEM AND METHOD FOR DYNAMIC, CARDIAC PHASE-RESOLVED QUANTITATIVE LONGITUDINAL RELAXATION PARAMETER MAPPING," which is herein incorporated by reference in its entirety.

STATEMENT REGARDING FEDERALLY SPONSORED RESEARCH

This invention was made with government support under HL111410 and EB015894 awarded by National Institutes of Health. The government has certain rights in the invention.

BACKGROUND

Cardiovascular MRI (CMR) can play a significant role in the diagnosis, staging, and monitoring of numerous ischemic and non-ischemic cardiomyopathies. Recently, parameter mapping in the heart has expanded the CMR toolbox, enabling the detection of diffuse pathologies and quantitative diagnosis. Among quantitative imaging technologies, myocardial T1 mapping has shown promising diagnostic and prognostic value in a wide range of diseases.

Early techniques for quantification of the longitudinal relaxation time (T1) in the heart have employed continuous imaging using equidistant FLASH excitations, following an initial inversion pulse, as originally proposed by D. C. Look and D. R. Locker in "Time Saving in Measurement of NMR and EPR Relaxation Times," *Review of Scientific Instruments*, 1970; 41:250-251. This technique allowed regional estimation of the T1 time by evaluating separate regions-of-interest in each cardiac cycle.

For voxel-wise quantification, the Modified Look-Locker Inversion recovery sequence ("MOLLI") was introduced, which performed single-shot imaging triggered to the end-diastolic quiescence in a Look-Locker type inversion-recovery experiment, as described by D. R. Messroghli, et al., in "Modified Look-Locker inversion recovery (MOLLI) for high-resolution T1 mapping of the heart," *Magnetic resonance in Medicine*, 2004; 52(1):141-146. The MOLLI pulse sequence enabled spatially-resolved quantification of the T1 time as a parameter map (T1 mapping) and established widespread use of quantitative CMR. Other imaging sequences, based on inversion or saturation recovery, or a combination of both, have been subsequently introduced for myocardial T1 mapping, each offering a distinct profile of advantages and disadvantages.

Myocardial T1 maps are conventionally acquired at a single end-diastolic phase. Recently, quantitative imaging during systole has been introduced, promising reduced partial volume effects, as well as increased resilience to heart-rate variability. Also, imaging throughout the cardiac cycle using variable flip-angle steady-state acquisitions has been explored for quantitative mapping in a preclinical mouse study, as described by B. F. Coolen, et al., in "Three-dimensional T1 mapping of the mouse heart using variable flip angle steady-state MR imaging," *NMR Biomed*, 2011; 24(2):154-162. However, due to limitations in terms of B1+ correction in the sequence proposed by B. F. Coolen, et al., quantitative T1 times were only derived at the end-diastolic phase.

Quantitative analysis of the T1 time in the myocardium conventionally entails manually delineating the myocardium from the surrounding blood pools. Hence, consistent contouring of the myocardium is important for the reproducibility of cardiac T1 measurements. However, sub-epicardial fatty infiltrations, myocardial crypts, trabeculae, and other structures have previously been shown to hamper the identification of the blood myocardial interface in single-phase cardiac images. Better temporal resolution, or the ability to view the changes in these structures over the cardiac phase, may facilitate differentiation.

SUMMARY OF THE DISCLOSURE

The present disclosure addresses the aforementioned drawbacks by providing a method for producing a map of a longitudinal relaxation parameter for a tissue of a subject using a magnetic resonance imaging ("MRI") system. The method includes establishing a selected magnetization state in the tissue of the subject using the MRI system and, after the selected magnetization state is established, applying a T1-preparation RF pulse to generate inverted magnetization in the tissue of the subject, which may be partially or completely inverted magnetization. While the inverted magnetization in the tissue of the subject is recovering back to the selected magnetization state, a data set is acquired at each of a plurality of different cardiac phases by sampling k-space in a k-space segment. The magnetization is then inverted again and more data are acquired for a selected number of inversion recovery periods, such that a plurality of data sets are acquired for each of the plurality of different cardiac phases. Images are reconstructed from the plurality of data sets and a map of the longitudinal relaxation parameter is produced by fitting the images to a parametric signal model that at least includes a parameter associated with the longitudinal relaxation parameter and another parameter associated with an inversion efficiency.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for producing quantitative maps of a longitudinal relaxation parameter, such as a longitudinal relaxation time ("T1"), using magnetic resonance imaging ("MRI"). The present disclosure provides a pulse sequence and imaging method for cardiac phase-resolved myocardial T1 mapping. More particularly, the present disclosure provides a pulse sequence and quantitative reconstruction technique that allows for dynamic T1 mapping of multiple different cardiac phases, which can also then be used to create a quantitative video of a heart-beat.

The pulse sequence described here employs an initial inversion pulse and subsequent imaging with spoiled gradient echoes for a given number of cardiac phases. As a result, acquisition of multiple k-space lines per heart-beat and per cardiac phase can be achieved. Imaging readout is repeated for multiple heart-beats after the inversion pulse, until a pulsed steady-state is reached. Hence, for each cardiac phase, k-space data are acquired with multiple inversion times. In some instances, to maintain continuous image excitation, dummy RF excitations with no imaging readout may be played after the given number of cardiac phases is acquired and until the detection of the following R-wave for each heart-beat.

The method described here, which can be referred to as a TempOrally-resolved Parametric Assessment of Z-magnetization recovery ("TOPAZ") method, implements a contiguous spoiled gradient echo readout (e.g., a fast low-angle shot, or "FLASH," pulse sequence) after magnetization inversion from a pulsed steady-state. Using this sequence, segmented k-space data are acquired over multiple heart beats, before reaching steady-state. As a result, the T1 recovery curve is sampled for each cardiac phase at multiple time points separated by an R-R interval.

Based on the data acquired with this pulse sequence, joint T1 and B1+ (transmit radio frequency) estimation can be performed for reconstruction of cardiac phase-resolved T1 and B1+ maps. For instance, B1+ correction can be performed in an integrated manner using the inversion-efficiency coefficient of a rectangular radio frequency ("RF") inversion pulse.

The present disclosure thus provides for temporally and spatially resolved mapping of the native myocardial T1 times, and also for integrated B1+ correction. As will be described below, acquisition parameters can be selected to yield optimal T1 mapping precision based on numerical simulations. With this method, in vivo imaging can be performed in a single breath-hold acquisition to provide a quantitative measurement of myocardial T1.

Figure 1:
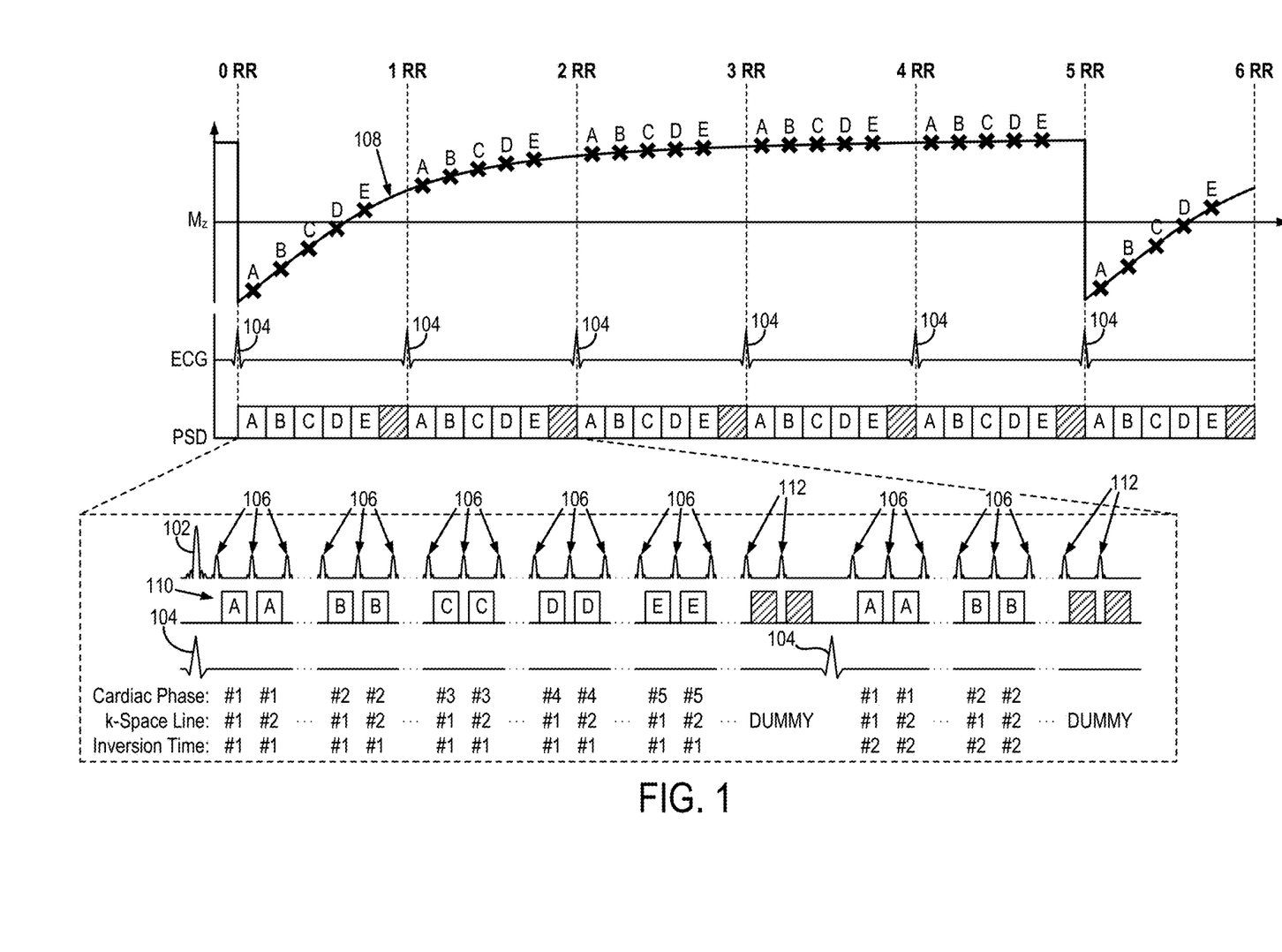
FIG. 1 is an example pulse sequence diagram for a temporally resolved parametric assessment of z-magnetization recovery pulse sequence.

A pulse sequence diagram for an example implementation of the TOPAZ acquisition described in the present disclosure is shown in FIG. 1. The signal is first driven to a selected magnetization state. In general, the selected magnetization state is a well-defined state, such as a state that can be analytically described in an image reconstruction and that is reproducible from segment-to-segment. As non-limiting examples, the selected magnetization state can be a pulsed or other steady-state, thermal equilibrium, or a desired level of saturation (e.g., total saturation in a particular tissue). In one example implementation, the acquisition begins with continuous FLASH imaging pulses to drive magnetization to a pulsed steady-state.

An initial T1-preparation RF pulse 102 is then applied following, or contemporaneous with, the detection of a physiological trigger event to generate inverted magnetization, which may be partial or complete inverted magnetization. The T1-preparation RF pulse 102 can thus have a flip angle of 180 degrees in some instances, or less than or more than 180 degrees in other instances. For example, the flip angle of the T1-preparation RF pulse 102 can be 170 degrees to provide near complete inversion of magnetization in the selected magnetization state. As one specific and non-limiting example, the magnetization inversion is performed from a steady-state signal using a rectangular hard pulse for the T1-preparation RF pulse 102.

The physiological trigger event can be an R-wave 104, or other signal feature of an electrocardiogram ("ECG") signal measured from the subject being imaged. In other examples, the physiological trigger event can be based on other physiological signals, including pulse oximetry signals, respiratory signals, self-gating signals, and so on.

Following this initial magnetization inversion, FLASH pulses 106 are continuously played to allow for the sampling of an apparent T1 recovery curve 108. The k-space readouts 110 are segmented across several cardiac phases for sufficient temporal resolution. As shown in FIG. 1, data are acquired during five different cardiac phases in each heart-beat, which are labeled as cardiac phases "A," "B," "C," "D," and "E." Multiple inversion times are sampled on the T1 recovery curve 108 until the selected magnetization state (e.g., pulsed steady-state, thermal equilibrium, desired level of saturation) is reached and another magnetization inversion is performed with the application of another T1-preparation RF pulse 102 to sample the next k-space segments. In the example shown in FIG. 1, magnetization inversion is repeated after 5 R-R intervals. This is repeated several times to fill k-space for each cardiac phase at five different inversion-times.

Using the technique described above, a k-space segment is acquired at each cardiac phase for several sample times on the T1 recovery curve 108, where the inversion times for a given cardiac phase are separated by the duration of the R-R interval. As stated above, after multiple heart-beats, the magnetization is driven to the selected magnetization state (e.g., pulsed steady-state, thermal equilibrium, desired level of saturation) and the acquisition of the next series of k-space segments starts with another T1-preparation RF pulse 102 played at the next physiological trigger event (e.g., the next R-wave 104).

To avoid deviation from the recovery curve in the presence of R-R interval variations (or other variations in the time interval between physiological trigger events), dummy pulses 112, with no corresponding signal readout, are played after the acquisition of a pre-determined number of cardiac phases until the detection of the subsequent physiological trigger event (e.g., R-wave 104).

Imaging during continuous RF excitation (e.g., FLASH excitation) allows sampling of an apparent longitudinal relaxation time, as will be described below. Moreover, knowledge of the pulse repetition time ("TR") and the flip-angle ("FA") can enable the determination of actual T1 values from the measured apparent longitudinal relaxation time. The flip-angle can be integratedly assessed when a non-adiabatic module is used for magnetization preparation. The efficiency of this pulse can then also be used to obtain a dynamic quantification of the effective B1+ transmit field strength and the effective FA.

Flip-angle and TR values can be selected based on numerical simulations to optimize the T1 mapping sensitivity of the pulse sequence. In one example, the number of k-space segments was selected to be between 8 and 12, depending on the heart-rate, to yield scan times between 17-23 s.

The magnetization signal during contiguous FLASH pulses can be described, by a three parameter inversion recovery model, $$M_z(t) = M_{SS} - (M_{SS} - M_z(0)) \cdot e^{-\frac{t}{T_1^*}}; \quad (1)$$

where $T_1^*$ is an apparent longitudinal relaxation time, which is a function of the flip-angle ("FA") and the repetition time ("TR"):

$$T_1^* = \left(\frac{1}{T_1} - \frac{1}{TR} \cdot \log(\cos(\alpha))\right)^{-1}; \quad (2)$$

where $\alpha$ is the flip-angle.

When the magnetization inversion is performed from the steady-state signal using a rectangular hard pulse, for an inversion flip angle of $\alpha_{inv}$, the initial signal can be described as, $$M_z(0) = M_{SS} \cos(\alpha_{inv}); \quad (3)$$

which leads to the magnetization, $$M_z(t) = M_{SS}(1 - (1 - \cos(\alpha_{inv}))) \cdot e^{-\frac{t}{T_1^*}}. \quad (4)$$

Thus, parameter quantification can be performed using a three-parameter least square fit, $$(\hat{A}, \hat{B}, \hat{T}_1^*) = \arg\min_{A,B,T_1^*} \sum_k \left\| S(t_k) - \left(A\left(1 - B \cdot e^{-\frac{t_k}{T_1^*}}\right)\right) \right\|^2; \quad (5)$$

where $t_k$ denotes the inversion time of the $k^{th}$ image and $S(t_k)$ is the corresponding signal for a given pixel location.

Because the "B" parameter describes the inversion efficiency, phase-resolved B1+ information can be estimated from the three-parameter fit. When a nominal inversion flip angle of $\alpha_{nom,inv}$ is utilized, the equation, $$\beta = \frac{\cos^{-1}(B-1)}{\alpha_{nom,inv}}; \quad (6)$$

results in the temporally-resolved, pixel-wise B1+ flip-angle scaling factor that can be used as a B1+ map. Accordingly, the actual excitation flip-angle can be derived from the three fit parameters as, $$\frac{\alpha_{exc}}{\alpha_{exc,nom}} \approx \frac{\alpha_{inv}}{\alpha_{inv,nom}} = \beta = \frac{\cos^{-1}(B-1)}{\alpha_{inv,nom}}. \quad (7)$$

Here, $\alpha_{exc,nom}$ is the nominal excitation flip-angle after compensation for slice-profile effects. As an example, given the signal along a non-constant slice profile, $\alpha(x)$, the nominal excitation flip-angle after compensation for slice-profile effects can be given as, $$\alpha_{slc} = \sqrt{\frac{\int_x M_{SS}(\alpha(x))\alpha(x)^2 dx}{\int_x M_{SS}(\alpha(x)) dx}}; \quad (8)$$

where, $$M_{SS}(\alpha) = \frac{\sin(\alpha)\left(1 - e^{-\frac{TR}{T_1}}\right)}{1 - \cos(\alpha)e^{-\frac{TR}{T_1}}}. \quad (9)$$

The T1 time can then be derived from the three fit parameters as, $$T_1 = \left(\frac{1}{\hat{T}_1^*} - \frac{1}{TR}\log(\cos(\alpha_{exc}))\right)^{-1} \quad (10)$$

$$\approx \left(\frac{1}{\hat{T}_1^*} - \frac{1}{TR}\log\left(\cos\left(\alpha_{exc,nom}\frac{\cos^{-1}(\hat{B}-1)}{\alpha_{inv,nom}}\right)\right)\right)^{-1}.$$

As one example, the three-parameter fitting in Eqn. (5) can be performed using a bounded parameter range for the inversion efficiency (e.g., [1.4, 2.4]) to avoid detrimental effects of outliers in the B1+ maps of late cardiac phases. When using $\alpha_{exc} = \alpha_{slc}$, it will be noticed that a value for T1 is used to calculate $M_{SS}(\alpha)$ via Eqn. (9). In these instances, T1 can be iteratively calculated using the following:

$$T_1 \approx \left(\frac{1}{\hat{T}_1^*} + \frac{\log(\cos(\alpha_{slc}))}{TR}\right)^{-1}; \quad (11)$$

initialized with $M_{SS}(\alpha)$ corresponding to the T1 value obtained without slice-profile correction.

The sensitivity of the parameter estimation described above is a function of the T1, the flip-angle, and the TR. In an example study, numerical Monte-Carlo simulations were performed to optimize the T1 time precision in dependence of the sequence parameters. The signal throughout the proposed sequence was simulated using Bloch-simulations with additive Rician-noise. Simulations were performed at an SNR of 30, with a heart-rate of 60 beats-per-minute ("bpm"), with no B1+ variations and a tissue T1 time of 1550 ms to resemble healthy myocardial tissue at a field strength of 3 T. The T1 time accuracy and T1 time precision were obtained as the mean and standard deviation of the estimated T1 across 1000 noise patterns, respectively.

To allow for sufficient recovery before the reinversion, the number of heart-beats between the inversion pulses in the simulated sequence was adapted to allow for recovery to at least 95% of the steady-state signal for each (TR, FA) pair and the given T1 value. This led to different scan times for different (TR, FA) settings, and restricted the applicable parameter range in order to avoid long breath-hold durations. The simulated parameter range spanned 1-20 degrees flip-angle in steps of 1 degree, and 3.5-15.0 ms TR in steps of 0.5 ms.

Figure 2:
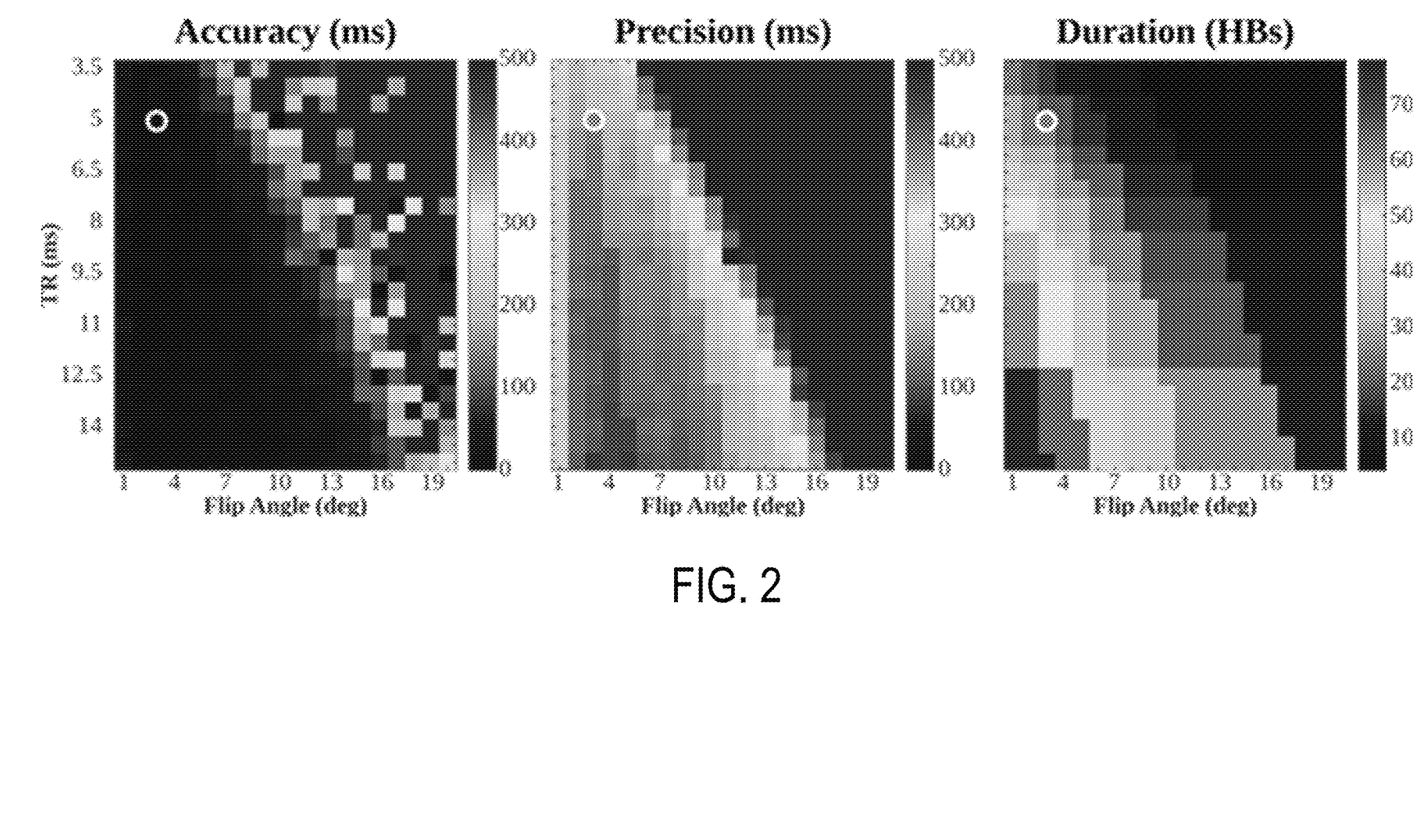
FIG. 2 shows simulation results depicting phantom accuracy, precision, and sequence duration as a function of repetition time ("TR") and flip angle, as assessed using Bloch-simulations with additive Rician-noise. The simulations illustrate that high flip-angles and short TRs may impair sensitivity to the T1 time and substantially compromise fit accuracy and precision. On the other hand, the simulations illustrate that long TRs and low flip-angles may result in long recovery periods leading to increased scan time. Based on these simulation results, a TR of 5 ms and a flip-angle of 3 degrees can be selected as a compromise between accuracy, precision, and scan duration.

FIG. 2 shows the precision, accuracy, and duration (i.e., scan time) of the proposed technique as functions of TR and flip-angle based on the numerical simulation described above. High flip-angles and short TRs cause rapid recovery to the steady-state magnetization, which prevents accurate T1 estimation and hampers the estimation precision. On the other hand, low flip-angles (e.g., those well below the Ernst angle) result in compromised T1 mapping precision due to insufficient imaging SNR. Long TRs increase the duration of the recovery and the steady-state signal, leading to improved precision, although at the cost of prolonged scan time. Based on these numerical simulations, as one example, a TR of 5 ms and a flip angle of 3 degrees can be chosen as a balanced trade-off between T1 mapping precision and scan time. It will be appreciated that other acquisition parameters can also be selected taking into consideration the trade-offs described above.

Figure 3:
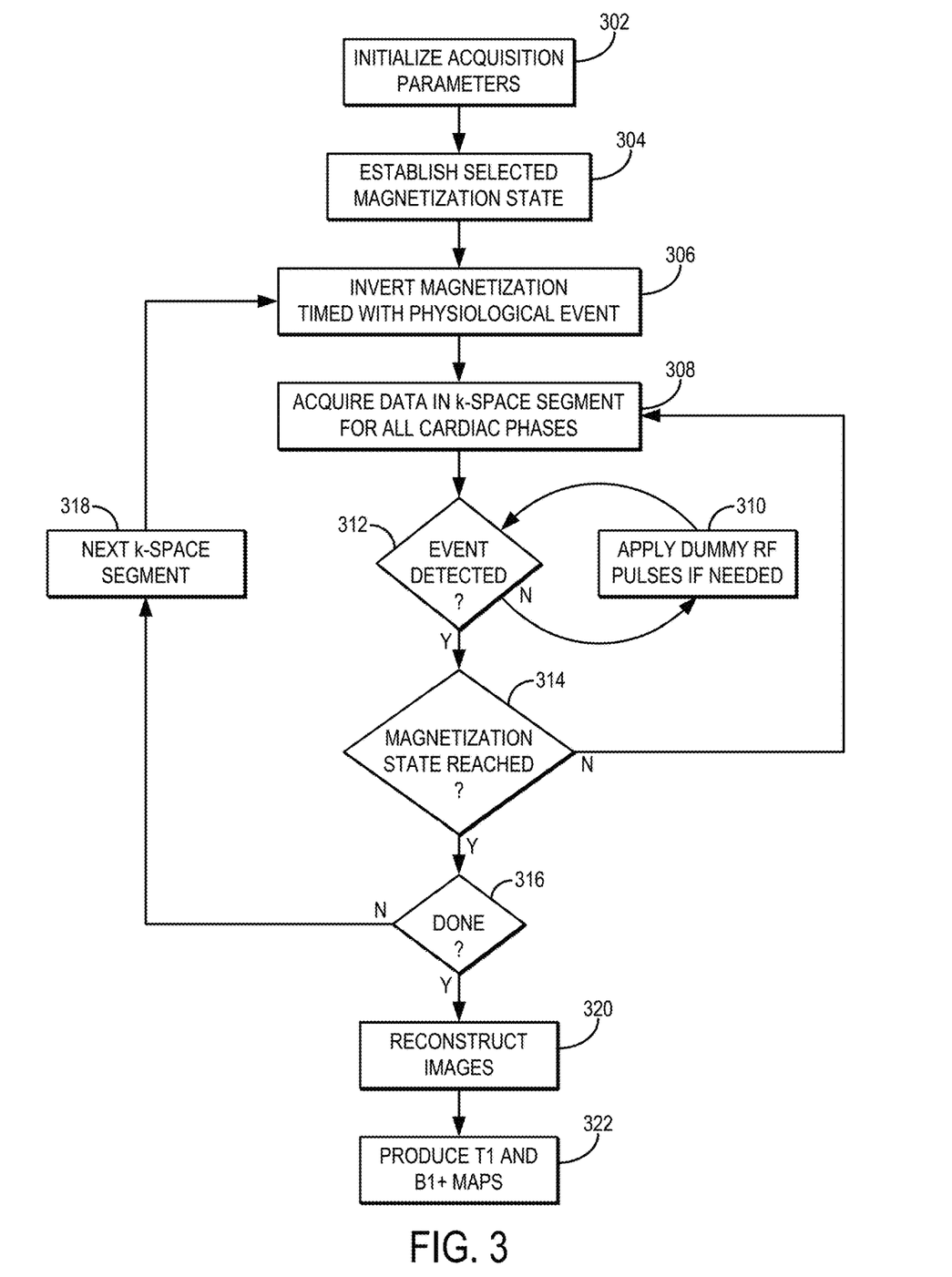
FIG. 3 is a flowchart setting forth the steps of an example method for producing a T1 map using a temporally resolved parametric assessment of z-magnetization recovery pulse sequence

Referring now to FIG. 3, a flowchart is illustrated as setting forth the steps of an example method for producing a quantitative T1 map using an MRI system. The method includes initializing acquisition parameters for the pulse sequence, as indicated at step 302. For instance, acquisition parameters such as flip angle, repetition time, the number of k-space segments (and corresponding number of cardiac phases) to acquire in each inversion recovery period, and the number of inversion recovery periods (and corresponding number of T1-preparation RF pulses to be applied) are selected. In one example, the flip angle may be 3 degrees, the repetition time may be 5 milliseconds, the number of k-space segments to be acquired in each inversion recovery period may be selected from a range of 8-12, and the number of inversion recovery periods may be 5.

The method then includes establishing a selected magnetization state (e.g., a pulsed or other steady-state, thermal equilibrium, a desired level of saturation) in a tissue of a subject to be imaged, as indicated at step 304. For example, steady-stage magnetization can be established by applying a series of continuous RF pulses with a low flip angle (e.g., continuous FLASH imaging pulses). After the selected magnetization state is established, the magnetization is inverted, as indicated at step 306, to generate inverted magnetization, which may be fully or partially inverted. For example, the magnetization is inverted by applying a T1-preparation RF pulse with the MRI system. The magnetization inversion is timed to be contemporaneous with, or to otherwise follow, the detection of a physiological trigger event measured from the subject. As one example, the physiological trigger event can be the detection of an R-wave, or other features, in an ECG signal measured from the subject. In other examples, the physiological trigger event can be measured from other physiological signals, such as pulse oximetry signals, respiratory signals, self-gating signals, and so on.

While the magnetization is recovering, the T1 recovery curve is sampled by acquiring data in multiple different k-space segments at a corresponding multiple different cardiac phases. Thus, data are acquired in a k-space segment across multiple cardiac phases, as indicated at step 308. As an example, the data are acquired using a series of spoiled gradient acquisitions with a low flip angle (e.g., using a FLASH acquisition scheme). After the selected number of acquisitions has been performed for the k-space segment and the cardiac phases, dummy RF pulses with no corresponding signal acquisition may be played out, as indicated at step 310, until the detection of a physiological trigger event, as indicated at decision block 312. As mentioned above, the physiological trigger event may be the detection of an R-wave or other feature in an ECG signal measured from the subject. In other examples, the physiological trigger event can be based on other physiological signals, including pulse oximetry signals, respiratory signals, self-gating signals, and so on.

After detection of this physiological trigger event, a determination is made as to whether the selected magnetization state has been established again, as indicated at decision block 314. If not, then data are acquired in the same k-space segment for the next set of cardiac phases. Because these data are acquired at different time points in the magnetization recovery curve, they will be representative of different inversion times.

When the selected magnetization state is established again, as determined at decision block 314, a determination is made as to whether a stopping criterion has been established, as determined at decision block 316. As one example, the stopping criterion can be based on whether the selected number of k-space segments have been acquired across the selected number of inversion recovery periods. If the stopping criterion has not yet been satisfied, the next k-space segment is selected at step 318 and the magnetization is inverted again at step 306. Data for the next k-space segment are then acquired over multiple cardiac phases while the magnetization recovers back to the selected magnetization state, as described above. In some instances, the image acquisition can be repeated multiple times by playing the T1-preparation RF pulse at a different times within the heartbeat.

After data are acquired for all selected k-space segments and cardiac phases across the selected number of inversion recovery periods, images are reconstructed from the acquired data, as indicated at step 320. The reconstructed images are then fitted to a parametric signal model to jointly estimate T1 and B1+ maps, as indicated at step 322. For example, the images can be fitted to the parametric signal model shown in Eqn. (5) using a least squares fit. In general, the parametric model includes a parameter associated with the longitudinal relaxation time (or rate) and a parameter associated with the inversion efficiency. The parameter associated with the inversion efficiency can be used to estimate the B1+ map. This joint estimation of T1 and B1+ maps can provide B1+ adjusted correction of apparent longitudinal relaxation times (e.g., for $T_1^*$ maps). As noted above, the T1 maps can in some instances be estimated using a flip angle value that has been corrected for slice-profile effects.

Although a conventional image reconstruction can be used in step 320, in some implementations a multi-scale locally low-rank noise reduction can be used in an iterative reconstruction algorithm.

As one example, for a fixed pixel location, the LLR approach can extract patches of size $m_1 \times m_2$, whose top left corner is at that pixel throughout the series of N images. These patches, which are positioned at the given pixel, are then vectorized and these vectors are put together to form a Casorati matrix, whose dimension is $m_1 m_2 \times N$. Due to redundancies in the image series that acquire the same anatomy over time and/or through contrast changes, this Casorati matrix can be represented accurately by a low-rank matrix, which can be enforced via singular value thresholding. The process is then repeated for other pixels to cover the whole image in-plane.

As another example, alternating between enforcing consistency with the acquired k-space data, and the LLR regularization of the images is avoided, while exploiting noise information that can be derived from the raw k-space data. To this end, an image reconstruction, which may be a parallel imaging reconstruction, in SNR units is performed. This initial reconstruction allows for the underlying noise distribution in the reconstruction to correspond a normal distribution. Following the extraction of the relevant local patches into a Casorati matrix, singular value thresholding can be performed. Because the reconstruction is in SNR units, the threshold parameter can be calculated analytically from the singular value distribution of a Gaussian random matrix, which follows a Marchenko-Pastur distribution, thereby eliminating the need for a heuristic parameter selection process. This process can be repeated for overlapping patches to avoid blocking artifacts, where patches are shifted by half a patch size in each direction.

A multi-scale denoising approach is then implemented in this example. In general, multi-scale approaches can include changing patch sizes or using a quad-tree structure. As one example, multiple patch sizes, $m_1^{(k)} \times m_2^{(k)}$, with their corresponding regularization parameters, $\lambda_{MP}^{(k)}$, can be used. As noted, the regularization parameters can be derived from a Marchenko-Pastur distribution, but in other examples different regularization parameters can also be used. Letting $R_{m,n}^P$ be the operator that extracts the m×n block whose top-left corner is at pixel location, p, into a Casorati matrix, and letting Y be the noisy image series, the following problem can be solved, $$\min_X \sum_p \sum_k \left[ \frac{1}{2} \left\| R_{m_1^{(k)},m_2^{(k)}}^P (Y - X) \right\|_F^2 + \lambda_{MP}^{(k)} \left\| R_{m_1^{(k)},m_2^{(k)}}^P (X) \right\|_* \right]. \quad (12)$$

As one example, the problem in Eqn. (12) can be solved using a projection onto convex sets ("POCS") technique.

As still another example, a locally low-rank tensor regularization can be used on local patches to enable the reconstruction of high-resolution quantitative images. The data acquired using the data acquisition techniques described in the present disclosure can be treated as a four-dimensional data structure, m(x,y,t,c), where (x,y) is the discrete spatial location, t is the cardiac phase, and c is different $T_1$ contrasts. Data acquired in k-space is given as, $$y(t,c) = E_{t,c}(m(x,y,t,c)) + n(t,c); \quad (13)$$

for $t=1, \ldots, T$ and $c=1, \ldots, C$, and where $E_{t,c}: \mathbb{C}^{M \times N} \to \mathbb{C}^P$ is the measurement system, including a partial Fourier matrix and the sensitivities of the receiver coil array, if one is used; $n(t,c) \in \mathbb{C}^P$ is the measurement noise; t is the cardiac phase; c is the contrast weighting; and x and y are the discrete spatial locations.

The four-dimensional data set, m(x,y,t,c) can be naturally represented as a fourth-order tensor, $$m = \sum_{r=1}^{R} a_r \otimes b_r \otimes c_r \otimes d_r \Leftrightarrow m(i,j,k,l) = \sum_{r=1}^{R} a_r(i) b_r(j) c_r(k) d_r(l); \quad (14)$$

where ⊗ represents the outer product, and R represents the rank of the tensor, m, the minimum number of rank one tensors needed to synthesize m as their sum. Finding the rank of a tensor is an NP-hard problem, with an upper bound given by min{MNT,MNC,MTC,NTC}.

Tucker and PARAFAC decompositions are two main approaches in low-rank tensor approximation. PARAFAC decomposition uniquely factorizes a tensor into a sum of rank one tensors, whereas Tucker decomposition factorizes a tensor into a core tensor multiplied by a matrix along each mode. Of these two approaches, the Tucker model is typically used for compression applications, and applied to the context of the image reconstruction problem presented here would include choosing four mode ranks, as it assumes low rank in each mode. PARAFAC is a direct low-rank decomposition that is mostly used for latent signal estimation, and uses a single tensor rank parameter.

In some applications of tensor regularization to MRI, the regularization can be performed globally. A global approach is suboptimal, however, because the imaging field-of-view often contains multiple structures with different functional and contrast properties. For instance, the chest wall and back contain stationary tissue that is high in fat, which has a very short T1 (<250 ms). The heart muscle (myocardium), on the other hand, contracts and expands substantially through the cardiac cycle and has a longer T1 (approximately 1500 ms). The blood pools also move and have even longer T1 (>2000 ms). Thus, it is hard to capture all the information in a few rank-1 components.

When using the methods described in the present disclosure, a tensor regularization can be implemented with small local patches in the spatial domain, which are modeled as low-rank tensors. This technique increases the likelihood that a patch will contain only tissue types that are related in function and contrast, instead of containing a large number of tissue types with varying properties.

As one example of a low-rank tensor-based regularization, images are first reconstructed, which may be performed using conventional or parallel image reconstruction. For instance, parallel imaging can be applied to each of a number of contrast weightings (e.g., C=5) and cardiac phases (e.g., T=11) individually to avoid or otherwise mitigate temporal blurring, contrast blurring, or both, in the reconstructed images. In other instances, a regularized image reconstruction can be implemented, where the regularization is provided by the tensor regularization now described.

Tensor regularization can be implemented to reduce the noise amplification due to the image reconstruction (e.g., the noise amplification due to linear parallel imaging reconstruction) in post-processing. One example of low-rank tensor factorization for noise reduction of a four-dimensional noisy tensor, X, can be carried out by solving the following problem:

$$\min_{\{a_r, b_r, c_r, d_r\}_{r=1}^{R}} \left\| X - \sum_{r=1}^{R} a_r \otimes b_r \otimes c_r \otimes d_r \right\|_F^2. \quad (15)$$

In some implementations, instead of solving the above least squares problem, which is non-convex, an alternating least squares ("ALS") approach can be used. In such instances, ALS solves for $\{a_r\}$ by fixing $\{b_r\}$, $\{c_r\}$, and $\{d_r\}$ so that the problem becomes (conditionally) linear. The procedure can then be repeated for the other components until a stopping criterion is met.

Thus, described here is a pulse sequence and corresponding imaging method for acquiring cardiac phase resolved native T1 maps of the myocardium, with integrated B1+ quantification. The methods described in the present disclosure can provide T1 and B1+ maps at a temporal resolution of up to 40 ms in a single breath-hold. The sequence parameters for the TOPAZ T1 mapping sequence described in the present disclosure can be optimized numerically, as described above.

Native myocardial T1 mapping is an emerging tool, establishing itself in the CMR sequence portfolio for diagnosis, risk stratification, and prognosis of numerous cardiomyopathies. Different tissue types, such as muscle, blood and fat, exhibit severely distinct T1 characteristics and need to be carefully delineated in order to maximize the diagnostic quality of T1 mapping.

T1 mapping during systole was proposed to increase the readily evaluable myocardial area and to facilitate manual contouring. Recently, blood-suppressed myocardial T1 mapping was also introduced, to eliminate contamination of the myocardial signal by the neighboring blood pool. Both approaches yield increased resilience to region-of-interest placement and decreased observer variability.

It is contemplated that the TOPAZ technique described in the present disclosure can further increase the diagnostic confidence in myocardial T1 maps by presenting quantification at multiple phases throughout the cardiac cycle. By quantifying T1 throughout the cardiac cycle rather than in a single cardiac phase, the delineation of blood and sub-endocardial fat and altered T1 times other observed in a single cardiac phase can be substantiated by cross-comparison throughout the cardiac cycle. This might be particularly useful in diseases that display reduced myocardial wall thickness, such as dilated cardiomyopathy, or in pathologies that form complicated focal/diffuse scar patterns, such as in HCM or amylodosis.

Conventional myocardial T1 mapping methods utilize single-shot imaging over a window of 200-250 ms to allow the acquisition of a single T1-weighted snap-shot of the heart per heart-beat. This temporal resolution is sufficient for imaging the left-ventricular myocardium during the end-diastolic quiescence in most patients and healthy volunteers; however, that temporal resolution is often insufficient to quantify highly mobile extra myocardial structures, such as cardiac tumors, including myxomas or thrombi. The methods described in the present disclosure enable imaging at a temporal resolution of up to 40 ms. Hence, the methods described in the present disclosure can be used to extend the applicability of T1 quantification to extra-myocardial structures, potentially easing non-invasive characterization or classification of cardiac masses, such as myxomas or other tumors.

The accurate T1 quantification provide by the method described in the present disclosure implements imaging of the magnetization during the approach to the pulsed steady-state. Due to non-rigid cardiac motion, myocardial tissue that is not subjected to the previous excitation pulses may move into the imaging plane and corrupt the signal. In these instances, increased slice thickness and a flat slice profile can be used to reduce sensitivity of the edges of the slice excitation to through-plane motion. Furthermore, three dimensional imaging might be used to provide excitation of the entire cardiac volume. However, the corresponding increase in acquisition time may then require using respiratory motion compensation if the acquisition cannot be performed in a single breath-hold for the subject.

Figure 4:
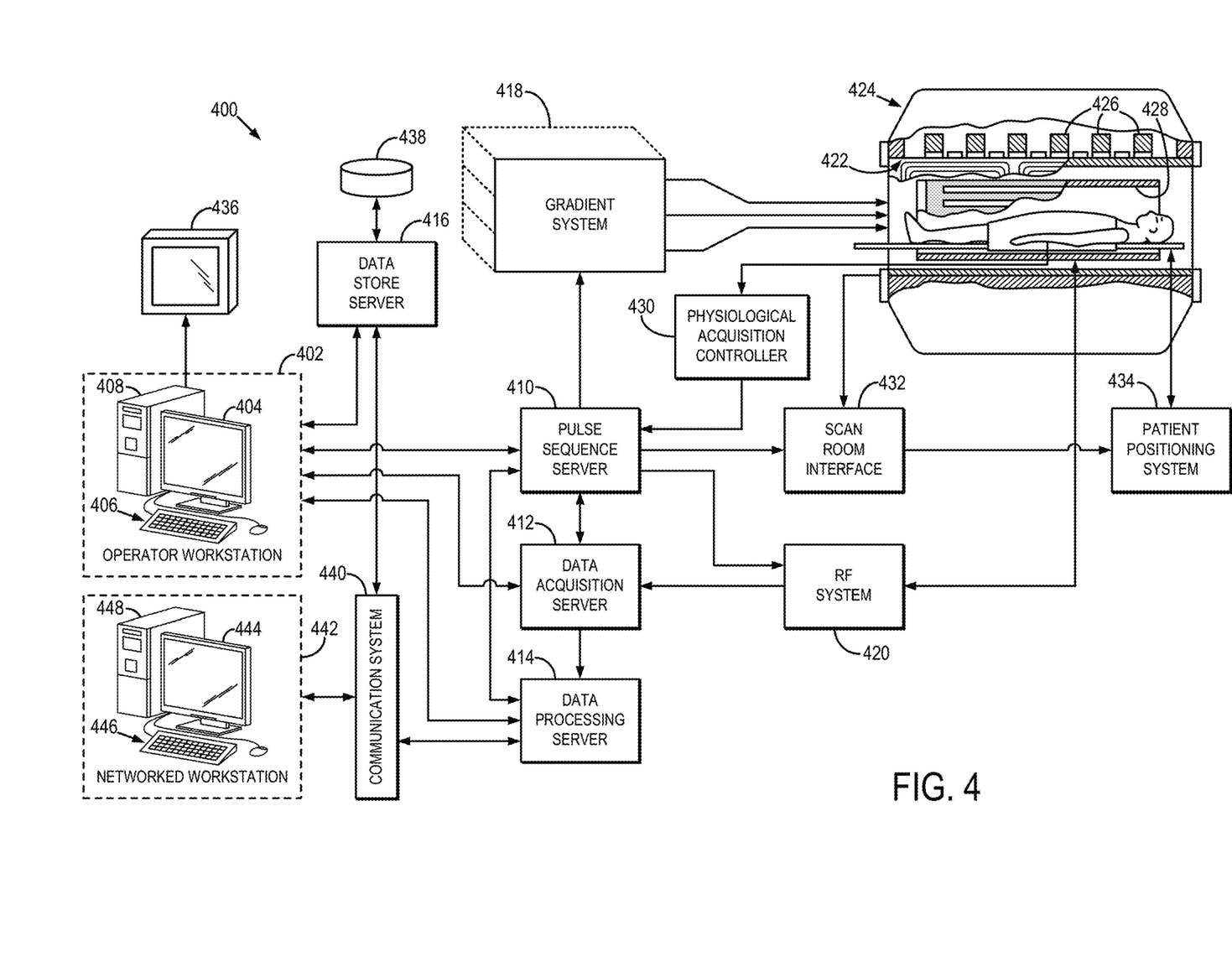
FIG. 4 is a block diagram of an example magnetic resonance imaging ("MRI") system that can implement the methods described in the present disclosure.

Referring particularly now to FIG. 4, an example of an MRI system 400 that can implement the methods described here is illustrated. The MRI system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MRI system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections.

The pulse sequence server 410 functions in response to instructions provided by the operator workstation 402 to operate a gradient system 418 and a radiofrequency ("RF") system 420. Gradient waveforms for performing a prescribed scan are produced and applied to the gradient system 418, which then excites gradient coils in an assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2}; \tag{16}$$

and the phase of the received magnetic resonance signal may also be determined according to the following relationship:

$$\varphi = \tan^{-1}\left(\frac{Q}{I}\right). \tag{17}$$

The pulse sequence server 410 may receive patient data from a physiological acquisition controller 430. By way of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data is not lost by data overrun. In some scans, the data acquisition server 412 passes the acquired magnetic resonance data to the data processor server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MRI system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

The present disclosure has described one or more preferred embodiments, and it should be appreciated that many equivalents, alternatives, variations, and modifications, aside from those expressly stated, are possible and within the scope of the invention.

The invention claimed is:

1. A method for producing a map of a longitudinal relaxation parameter for a tissue of a subject using a magnetic resonance imaging (MRI) system, the steps of the method comprising:
   (a) establishing a selected magnetization state in the tissue of the subject using the MRI system;
   (b) after the selected magnetization state is established, applying a T1-preparation RF pulse to generate inverted magnetization in the tissue of the subject;
   (c) while the inverted magnetization in the tissue of the subject is recovering and until the selected magnetization state is established again, acquiring a data set at each of a plurality of different cardiac phases by sampling k-space in a k-space segment;
   (d) repeating steps (b) and (c) for a selected number of inversion recovery periods such that a plurality of data sets are acquired for each of the plurality of different cardiac phases;
   (e) reconstructing images from the plurality of data sets;
   (f) producing the map of the longitudinal relaxation parameter by fitting the images to a parametric signal model that at least includes a parameter associated with the longitudinal relaxation parameter and another parameter associated with an inversion efficiency; and
   wherein step (f) includes jointly estimating the longitudinal relaxation parameter map and a transmit RF field (B1+) map by fitting the images to the parametric signal model.

2. The method as recited in claim 1, wherein the T1-preparation RF pulse is applied at a time based on a detection of a physiological trigger event.

3. The method as recited in claim 2, wherein the physiological trigger event is an occurrence of an R-wave in an electrocardiograph (ECG) signal measured from the subject.

4. The method as recited in claim 3, wherein the T1-preparation RF pulse is applied when the R-wave in the ECG signal is detected.

5. The method as recited in claim 1, wherein the selected magnetization state is a pulsed steady-state and is established in step (a) by applying a series of continuous RF pulses to the tissue of the subject.

6. The method as recited in claim 5, wherein the series of continuous RF pulses comprises RF pulses having a flip angle less than 180 degrees.

7. The method as recited in claim 6, wherein the series of continuous RF pulses comprises RF pulses having a flip angle in a range of 1 to 20 degrees.

8. The method as recited in claim 1, wherein data in each data set are acquired by sampling k-space in the k-space segment using a data acquisition comprising a series of continuous RF pulses and a spoiled gradient readout.

9. The method as recited in claim 8, wherein the series of continuous RF pulses comprises RF pulses having a flip angle less than 180 degrees.

10. The method as recited in claim 9, wherein the series of continuous RF pulses comprises RF pulses having a flip angle in a range of 1 to 20 degrees.

11. The method as recited in claim 1, wherein step (c) further includes after acquiring each data set, applying a selected number of dummy RF pulses until a physiological trigger event is detected.

12. The method as recited in claim 11, wherein the physiological trigger event is an occurrence of an R-wave in an electrocardiograph (ECG) signal measured from the subject.

13. The method as recited in claim 11, wherein no data are acquired in response to the dummy RF pulses.

14. The method as recited in claim 1, wherein step (c) includes acquiring each data set for each of the plurality of different cardiac phases by sampling k-space in a different k-space segment.

15. The method as recited in claim 1, wherein the B1+ map is estimated based on the parameter associated with the inversion efficiency.

16. The method as recited in claim 1, wherein the T1-preparation RF pulse is an RF inversion pulse.

17. The method as recited in claim 1, wherein the selected magnetization state is one of a pulsed steady-state, a thermal equilibrium, or a desired level of saturation.

18. The method as recited in claim 1, wherein step (f) includes producing a plurality of longitudinal relaxation parameter maps.

19. The method as recited in claim 18, wherein the plurality of longitudinal relaxation parameter maps are temporally resolved longitudinal relaxation parameter maps.

20. The method as recited in claim 1, wherein step (e) includes reconstructing the images using an iterative reconstruction that is regularized in part using a multi-scale locally low-rank noise reduction.

21. The method as recited in claim 1, wherein step (e) includes reconstructing the images using an iterative reconstruction that is regularized in part using a low-rank tensor regularization.

22. A method for producing a map of a longitudinal relaxation parameter for a tissue of a subject using a magnetic resonance imaging (MRI) system, the steps of the method comprising:
  (a) establishing a selected magnetization state in the tissue of the subject using the MRI system;
  (b) after the selected magnetization state is established, applying a T1-preparation RF pulse to generate inverted magnetization in the tissue of the subject;
  (c) while the inverted magnetization in the tissue of the subject is recovering and until the selected magnetization state is established again, acquiring a data set at each of a plurality of different cardiac phases by sampling k-space in a k-space segment;
  (d) repeating steps (b) and (c) for a selected number of inversion recovery periods such that a plurality of data sets are acquired for each of the plurality of different cardiac phases;
  (e) reconstructing images from the plurality of data sets;
  (f) producing the map of the longitudinal relaxation parameter by fitting the images to a parametric signal model that at least includes a parameter associated with the longitudinal relaxation parameter and another parameter associated with an inversion efficiency;
  wherein the selected magnetization state is a pulsed steady-state and is established in step (a) by applying a series of continuous RF pulses to the tissue of the subject; and
  wherein the series of continuous RF pulses comprises RF pulses having a flip angle in a range of 1 to 20 degrees.

23. A method for producing a map of a longitudinal relaxation parameter for a tissue of a subject using a magnetic resonance imaging (MRI) system, the steps of the method comprising:
  (a) establishing a selected magnetization state in the tissue of the subject using the MRI system;
  (b) after the selected magnetization state is established, applying a T1-preparation RF pulse to generate inverted magnetization in the tissue of the subject;
  (c) while the inverted magnetization in the tissue of the subject is recovering and until the selected magnetization state is established again, acquiring a data set at each of a plurality of different cardiac phases by sampling k-space in a k-space segment;
  (d) repeating steps (b) and (c) for a selected number of inversion recovery periods such that a plurality of data sets are acquired for each of the plurality of different cardiac phases;
  (e) reconstructing images from the plurality of data sets;
  (f) producing the map of the longitudinal relaxation parameter by fitting the images to a parametric signal model that at least includes a parameter associated with the longitudinal relaxation parameter and another parameter associated with an inversion efficiency;
  wherein data in each data set are acquired by sampling k-space in the k-space segment using a data acquisition comprising a series of continuous RF pulses and a spoiled gradient readout,
  wherein the series of continuous RF pulses comprises RF pulses having a flip angle in a range of 1 to 20 degrees.

* * * * *